(12) United States Patent
Högfors et al.

(10) Patent No.: US 6,358,283 B1
(45) Date of Patent: Mar. 19, 2002

(54) IMPLANTABLE DEVICE FOR LENGTHENING AND CORRECTING MALPOSITIONS OF SKELETAL BONES

(76) Inventors: Christian Högfors, Box 156, 524 22 Herrljunga; Abbas Karladani, Pojkebo 13116, 444 96 Ödsmål, both of (SE)

( * ) Notice: Subject to any disclaimer, the term of this patent is extended or adjusted under 35 U.S.C. 154(b) by 0 days.

(21) Appl. No.: 09/579,412

(22) Filed: May 25, 2000

Related U.S. Application Data

(60) Provisional application No. 60/140,326, filed on Jun. 21, 1999.

(51) Int. Cl.$^7$ ................................................ A61F 2/28
(52) U.S. Cl. ................................ 623/23.47; 623/16.11
(58) Field of Search ........................... 623/23.28, 23.45, 623/23.47, 20.16

(56) References Cited

U.S. PATENT DOCUMENTS

| | | | |
|---|---|---|---|
| 3,591,010 A | * 7/1971 | Pall | 210/493 |
| 4,279,249 A | 7/1981 | Vert et al. | |
| 5,084,050 A | 1/1992 | Draenert | |
| 5,466,261 A | * 11/1995 | Richelsoph | 623/16 |
| 5,626,581 A | 5/1997 | Staehlin et al. | |
| 5,645,592 A | 7/1997 | Nicolais et al. | |

OTHER PUBLICATIONS

Abstract of U.S. Pat. No. 5,415,660; Publication Date: May 16, 1995 for Implantable Limb Lengthening Nail Driven By a Shape Memory Alloy; by Bechtold et al.

Abstract of U.S. Pat. No. 5,074,882; Publication Date: Dec. 24, 1991 for Progressive Elongation Centro–Medullar Nail; by Grammont et al.

Abstract of U.S. Pat. No. 5,505,733; Publication Date: Apr. 9, 1996 for Intramedullary Skeletal Distractor and Method; by Cole et al.

* cited by examiner

Primary Examiner—David J. Isabella
Assistant Examiner—Urmi Chattopadhyay
(74) Attorney, Agent, or Firm—Samuels, Gauthier & Stevens, LLP

(57) ABSTRACT

An implantable device for lengthening and correcting malpositions of skeletal bones, which device has an elongate shape comprising a first end, a second end, a length dimension and a cross-sectional dimension. The device further comprises a lengthening body for bringing the first and second ends into displacement from each other to a predetermined distance between each other after an activation. Thereby, the lengthening body comprises an absorbent body, which is arranged for bringing the first and second ends to the predetermined distance by means of a controlled swelling after the activation, while the length dimension increases more than the cross-sectional dimension. The implantable device can advantageously be implemented for lengthening and also for correcting rotational and angular malpositions of skeletal bones, for example in connection with stabilizing fractures, post-traumatic bone defects, bone shortenings, malpositions, congenital malformations, and bone defects after tumor surgery.

10 Claims, 4 Drawing Sheets

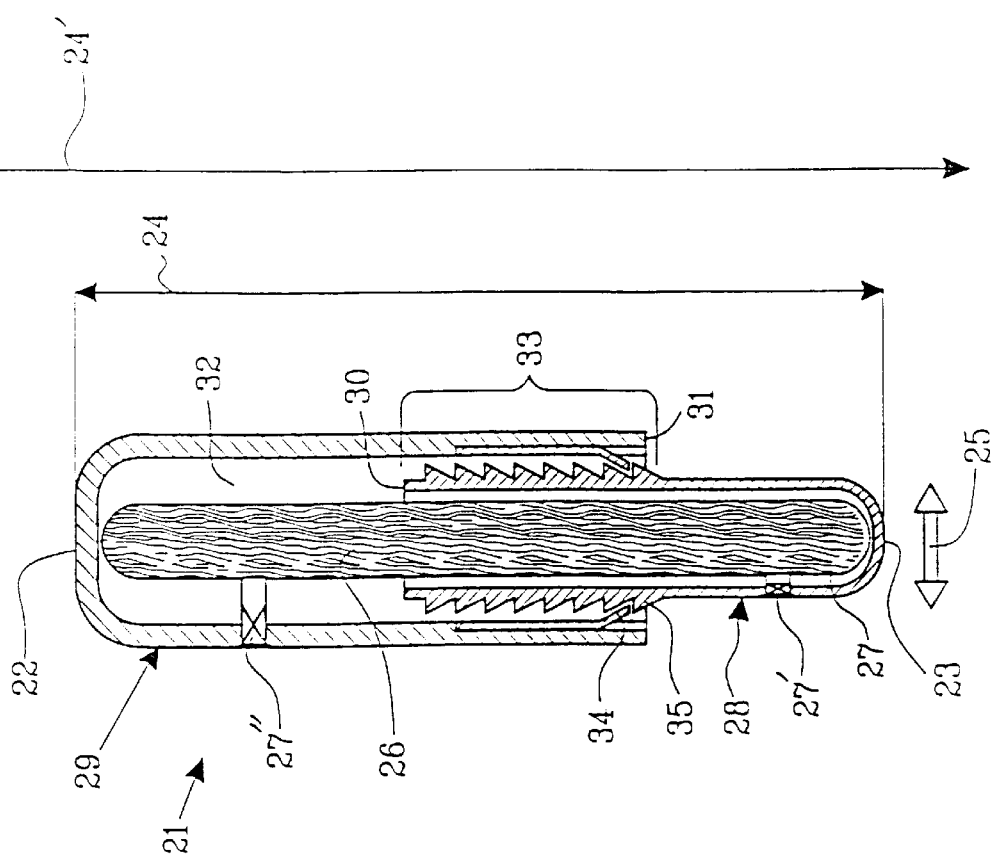
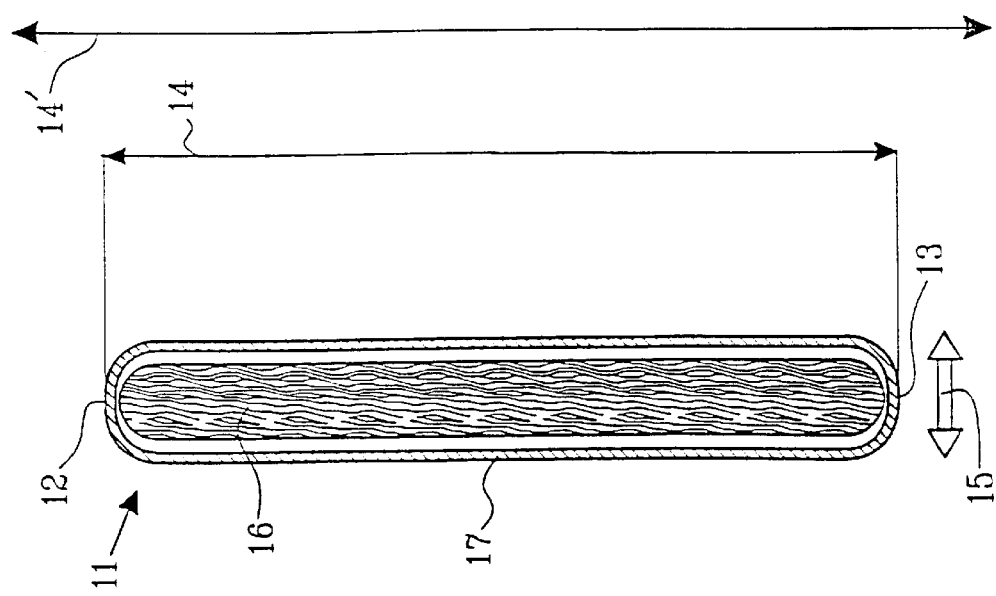

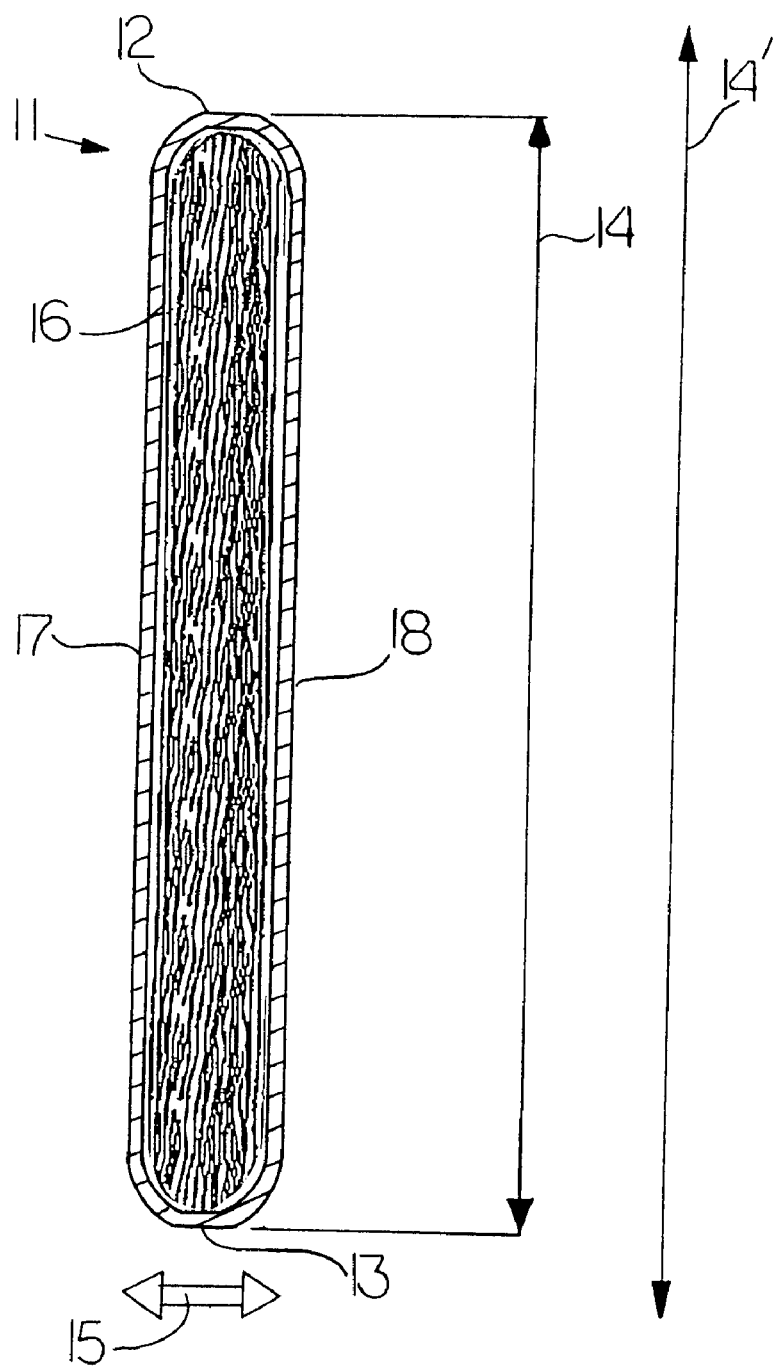
FIG. IA

IMPLANTABLE DEVICE FOR LENGTHENING AND CORRECTING MALPOSITIONS OF SKELETAL BONES

PRIORITY INFORMATION

This application claims priority from provisional application Ser. No. 60/140,326 filed Jun. 21, 1999.

TECHNICAL FIELD

The present invention pertains to the field of orthopedic surgery, and more specifically relates to an implantable device for lengthening, and also for correction of rotational and angular malpositions, of skeletal bones. The invention advantageously can be applied in connection with stabilization of fractures, post-traumatic bone defects, bone shortening, malpositions, congenital malformations and bone defects after tumor surgery.

BACKGROUND OF THE INVENTION

Within the field of orthopedic surgery, it is known to use implantable devices for stabilizing fractures, lengthening skeletal bones, or for correcting different malpositions.

Many of the previously known devices require that suitable attachments means are driven into the skeletal bone on both sides of the bone portion which is to be influenced, and that subsequently a screw assembly is applied between the attachment means, wherein a screw or the like acting on the screw assembly, alternatively on the attachment means, is allowed to protrude through the skin of the patient. Thereafter, by means of turning the screw, the length of the screw assembly can be influenced in accordance with an adapted lengthening scheme. Accordingly, in case it is desired to correct a malposition of a skeletal bone which for some reason occurs, by means of a surgical operation, a screw assembly of the above-described type can be applied at one side of the skeletal bone with the aid of two attachment means, whereafter the skeletal bone between the two attachment means can be cut off. By means of lengthening the screw assembly in accordance with the chosen lengthening scheme, a gradual ending of the skeletal bone in question can be obtained. Finally, after an appropriate healing time, the screw assembly, the screw and the attachment means can be removed by means of a surgical operation. In case only a linear lengthening is desired, several screw assemblies in parallel can be applied around the skeletal bone in question.

Furthermore, when stabilizing fractures, it is known to use intramedullary nails, which are inserted into the bone-marrow cavity of a tubular skeletal bone. During use, it is also know that such devices can be activated and/or controlled from the outside after the implantation and during lengthening action.

Accordingly, for example the patent publication U.S. Pat. No. 5,626,521 discloses a nail assembly for bone lengthening comprising a first nail body portion and a second nail body portion. The assembly farther comprises a power package inside either the first or the second nail body portion, wherein the power package comprises a power-supplied hydraulic pump which forces hydraulic fluid from a hydraulic fluid container and into a sealed chamber between the first and second nail body portions, thereby forcing the first nail portion to be extended longitudinally in relation to the second nail portion and increasing the length of the nail. It is also reported that the disclosed assembly may comprise a spring of a heat-sensitive memory material such as nitinol, and a heating system with a battery-powered electrical heater acting on the spring. According to U.S. Pat. No. 5,626,521, external activation and/or control of the assembly may be accomplished e.g. by means of providing the heating system with a timer or a suitable circuit for remote control which acts on the heating system.

Previously known arrangements for lengthening or correction of skeletal bones which require one or several permanent skin lead-throughs during the treatment time are associated with a large discomfort for the patient and a raised risk of infection.

The previously known implantable devices for lengthening and correction of skeletal bones which can be controlled from the outside, or which otherwise can be controlled without any permanent skin lead-throughs, often comprise a large number of mechanical and electronic components, and can be perceived as complicated or unnecessarily expensive.

When the external dimensions, the durability and the different lengthening properties are concerned, It may become expensive to tailor-make devices for each individual case in accordance with the prior art, since this often requires a number of the many different components to be re-dimensioned. Furthermore, when devices having small external dimensions arc concerned, problems with lack of internal space may arise.

SUMMARY OF THE INVENTION

Accordingly, a first object of the present invention is to provide a simple and reliable, implantable device for lengthening and correcting malpositions of skeletal bones, wherein the dimensions and the lengthening process of the device can be tailor-made in advance for the configuration and type of tubular skeletal bone in question into which the device is to be implanted, and where the device also can be designed with very small external dimensions thanks to its simple design.

The first object of the invention is achieved by means of the device having an elongate shape comprising a first end, a second end, a length dimension and a cross-sectional dimension, and the device further comprising a lengthening means for bringing the first and second ends into displacement from each other to a predetermined distance between each other after an activation. According to the invention, the lengthening means comprises an absorbent body, which is arranged for bringing the first and second ends to the predetermined distance by means of a controlled swelling after the activation while the length dimension increases more than the cross-sectional dimension.

A second object of the present invention is to provide an implantable device which, in addition to the above-mentioned advantages, also enables correction of rotational and angular malpositions of skeletal bones.

The second object of the invention is achieved by means of the absorbent body of the implantable device further comprising one or several stiffening elements and/or one or several swelling zones having a raised intrinsic swelling capacity in comparison to the remaining absorbent body, which arc arranged for controlling the swelling so that the first and second ends strive towards a predetermined angle in relation to each oilier after the activation.

Further object of the invention will become evident from the following description, while the features enabling these further objects to be achieved are evident from the attached, dependent claims.

BRIEF DESCRIPTION OF THE DRAWINGS

In the following, the invention will be described in greater detail with reference to the attached drawings, in which FIG. 1 schematically shows a sectional view through an implantable device according to a preferred embodiment of the invention, FIG. 1A schematically shows a sectional view through an implantable device according to an alternative embodiment of the invention, FIG. 2 schematically shows a sectional view through an implantable device according to an alternative embodiment of the invention, FIG. 3A schematically shows a sectional view through an implantable device according to a particularly preferred embodiment of the invention, before activation.

DETAILED DESCRIPTION OF PREFERRED EMBODIMENTS

Figure 3A:
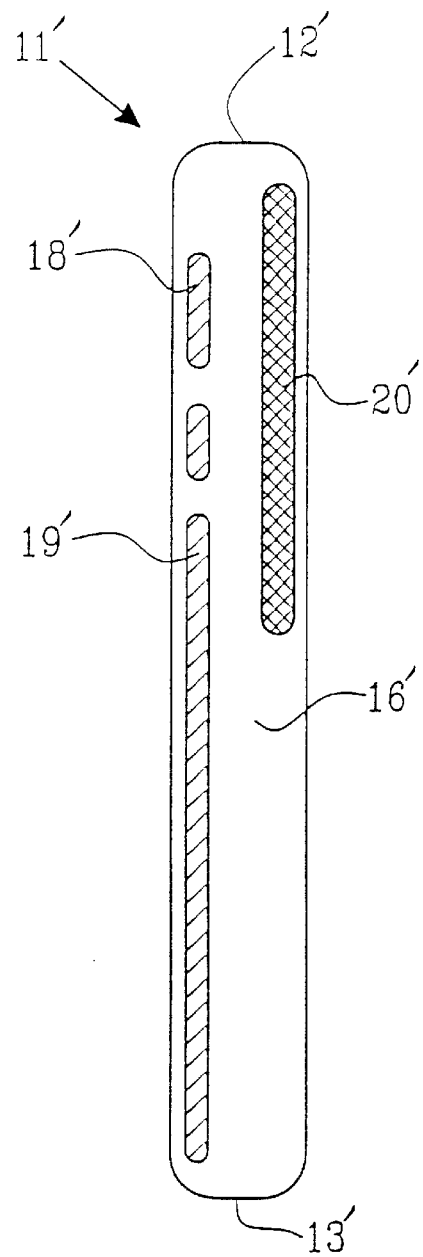
FIG. 3B schematically shows a sectional view through the implantable device in FIG. 3A, after motivation and subsequent swelling, and FIG. 4 schematically shows a sectional view through an implantable device according to another alternative embodiment of the invention.
Figure 3B:
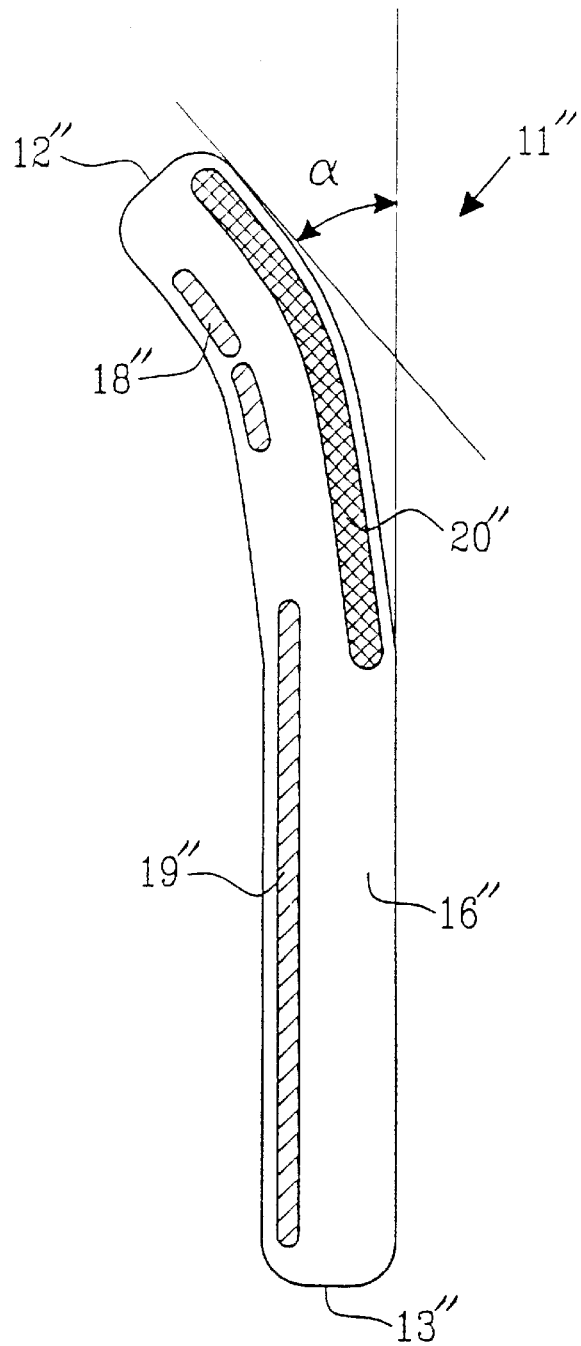

In the following, a particularly preferred embodiment, and a number of alternative and advantageous embodiments of an implantable device for lengthening and correcting malpositions of skeletal bones according to the invention will be described with reference to the attached FIGS. 1 to 4.

The implantable device 11; 11'; 21; 111 according to the invention has an elongate shape comprising a first end 12; 12'; 22; 112. a second end 13; 13'; 23; 113, a length dimension 14; 24; 114 and a cross-sectional dimension 15; 25; 115. Thereby, "cross-sectional dimension" e.g. refers to the outer diameter in case of a circle-cylindrical device, but can also refer to another cross-sectional dimension depending on the geometrical shape of the cross-section.

Furthermore, the device 11; 11'; 21; 111 comprises a lengthening means 16; 16'; 26; 116,216 for bringing the first 12;12'; 22; 112 and second 13; 13'; 23; 113 ends into displacement from each other to a predetermined distance 14'; 24'; 114' between each other after an activation. Thereby, "predetermined distance" refers to the maximum distance of the implantable device which is desirable after it has been Implanted into a tubular skeletal bone. The predetermined distance has to be adapted for each individual case.

According to the invention, and in the particularly preferred embodiment, the lengthening means comprises an absorbent body 16; 16'; 26; 116, which is arranged for bringing said first 12; 12'; 22; 112 and second 13; 13'; 23; 113 ends to the predetermined distance 14; 24'; 114' by means of a controlled swelling after the activation, while the length dimension 14; 24; 114 increases inure than the cross-sectional dimension 15; 25; 115.

In the particularly preferred embodiment of the implantable device 11', 11" according, to the invention, shown in FIGS. 3A (before activation) and 3B (after activation and swelling), the absorbent body 16', 16" comprises one or several stiffening elements 18', 18", 19', 19", and/or one or several swelling zones 20', 20" having a raised intrinsic swelling capacity in comparison to the remaining absorbent body 16', 16". Thereby, the stiffening elements and/or the swelling zones are arranged for controlling the swelling so that said first 12', 12" and second 13', 13" ends strive towards a predetermined angle α in relation to each other after the activation. Thereby, the stiffening elements 18', 18", 19', 19" advantageously are constituted of inserts of metal or plastic, while the swelling zones 20', 20" advantageously comprise a high content of superabsorbent. However, it is conceivable with embodiments with another choice of material, or where only stiffening elements or only swelling zones are present.

Accordingly, within the scope of the invention, it is conceivable with embodiments in which the first and second ends essentially are in the same plane (α≈0) before the swelling and are displaced in relation to the plane (α>0) by the swelling, or inversely, embodiments in which the two ends initially are displaced in relation to a plane (α>0) and are brought into the same plane (α≈0) by the swelling.

In one advantageous embodiment, the absorbent body 16; 16', 16" primarily is constituted of a matrix of thermosetting melamine formaldehyde plastic on a needled reinforcement material of HT-rayon. Thereby. HT-rayon refers to rayon fibers or filaments having a high tenacity. Furthermore, the absorbent body 16 advantageously comprises micro-crystalline cellulose as a filer. The absorbent body preferably has been compression-molded to its intended shape during heating. Within the scope of the invention, it is of course also conceivable with absorbent bodies with another matrix material, reinforcement material, or filler. Accordingly, the matrix material can consist of or comprise another polymeric resin suitable for the purpose, the reinforcement material can consist of or comprise another fiber material suitable for the purpose, and the filler can consist of or comprise a suitable superabsorbent, such as for example cellulose acetate.

In an alternative embodiment, in addition to an absorbent body of e.g. the type shown in FIG. 1, the device 21 further comprises first 28 and second 29 cylinder members having closed ends 22, 23 and opposite open ends 30, 31. Thereby, the open end 30 of the first cylinder member 28 is at toast partially slidably inserted into the open end 31 of the second cylinder member 29, so that the cylinder members 28,29 together form at least one internal cavity 32 within which the absorbent body 26 is arranged. Furthermore, a back stop device 33 is arranged between the open ends 30, 31 for enabling the first 22 and second 23 ends of the implantable device 21 to be irreversibly displaced to the predetermined distance 24' after the activation. Thereby "irreversibly" refers to the fact that the implantable device cannot be compressed in its longitudinal direction, but can only be extended until the first and second ends of the device have arrived at the above-mentioned predetermined distance between each other.

In another alternative embodiment, the device comprises valves 27', 27" for opening or closing a connection between the absorbent body 26 and the environment surrounding the device 21, wherein the valves 27', 27" are arranged for being controlled by means of radio waves, ultrasonic, induction or magnetic control when accomplishing the activation and/or a deactivation. This embodiment is particularly advantageous when the device according to the invention comprises cylinder members of the above-mentioned type which enclose the absorbent body, but it is also conceivable with embodiments where the absorbent body only is enclosed by a relatively impervious membrane through which the valve or valves are arranged.

In still another alternative embodiment, the back stop device 33 comprises at least one spring-loaded member 34 of one of the cylinder members which is arranged for mechanical engagement with a member provided with steps 35 of the other cylinder member. Thin type of back stop device is schematically depicted in the attached FIG. 2.

In still another alternative embodiment, the cylinder members are slidably arranged with seals (not shown)

against each other, wherein the internal cavity is divided into at least two portions by a stationary partition wall in which a connection having a check valve has been arranged.

Figure 4:
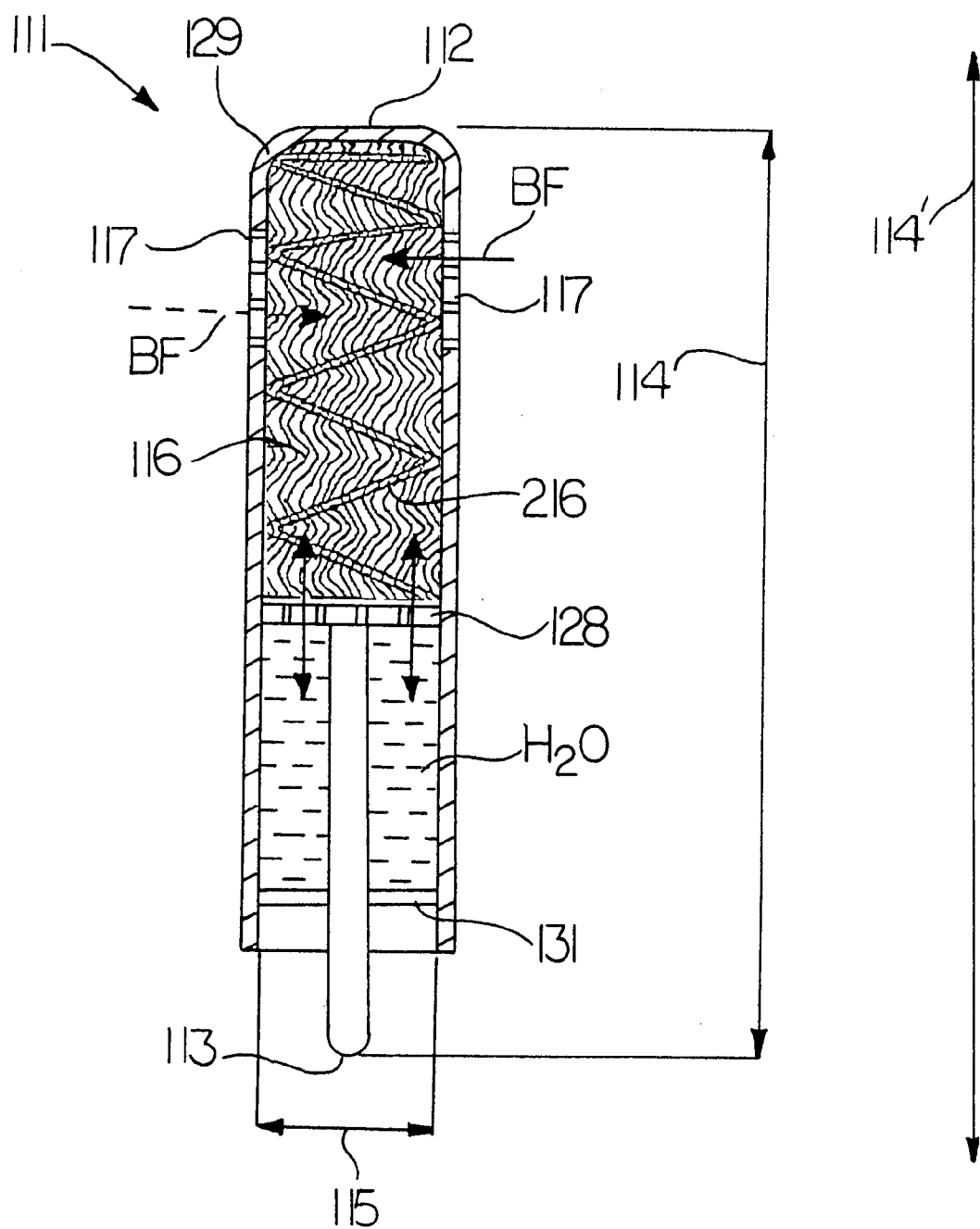

In another advantageous, alternative embodiment of the device according to the invention, illustrated in FIG. 4, the absorbent body 116 is accommodated within a cylindrical member 129 comprising water inlet means for allowing water transport into the absorbent body during the controlled swelling. In this embodiment, the second end 113 is connected to a piston means 128 arranged for sliding displacement within the cylindrical member 129 wherein at least one spring member 216 is embedded in the absorbent body 116 for exercising a lengthening force In cooperation with the absorbent body on the first 112 and second 113 ends during the controlled swelling. The spring member 216 is preferably a helical steel spring. However, it's also conceivable with embodiments with other geometrical spring shapes and/or materials.

In the alternative embodiment, the water inlet means can be constituted by one or several water-permeable portions 117 In the cylindrical member 129, by the piston means 128 being water-permeable, or by the piston means 128 consisting of a disc member with a plurality of axially extending through-apertures, which CW1 be accomplished e.g. by means of punching or laser cutting. If desired, the water inlet means can be constituted by the piston means comprising one or several nonreturn valves, for allowing water transport only in a direction towards the absorbent body.

In the alternative embodiment, as illustrated in FIG. 4, the cylindrical member 129 preferably is seated by a wall member 131 between the piston means 128 and the second end 113, thereby forming an internal cavity within the cylindrical member 129. The internal cavity is intended to be filled with an aqueous liquid H2O for providing at least a part of the water during the controlled swelling. It is also conceivable with embodiments in which opposing spring members (not shown) are provided on both sides of the piston moans 128 in order to facilitate the control of the lengthening course of the implantable device.

In the described alternative embodiment, the absorbent body 116 and the spring member(s) 216 are adapted for bringing the first 112 and second 113 ends to the predetermined distance by means of exercising a pressure together on the first and second ends after the activation which is larger than about 500 N/cm2. Furthermore, the water inlet means 117, 128 advantageously arc adapted to the remaining components 112, 116 of the implantable device 111, so that the water transport (into the absorbent body 116) during the controlled swelling generates a lengthening rate of about 1 mm/day. However, it is also conceivable with alternative embodiments with another pressure and/or lengthening rate.

In embodiments of the implantable device according to the invention where the absorbent body is enclosed by and stabilized by cylinder members of the above-discussed type, the absorbent body 26; 116 particularly advantageously comprises cellulose acetate or another superabsorbent. When the cylinder members 28; 29; 129 are concerned, they particularly advantageously are constituted of titanium. However, it is also conceivable with embodiments where the absorbent body comprises another suitable absorbent material, or where the cylinder members are made of another material suitable for insertion into a shaft of a bone.

In all embodiments of the implantable device, it is particularly advantageous that the absorption properties of the absorbent body 16; 16'; 16"; 26; 116 are adapted so that the activation can be accomplished by means of wetting with water originating from a body fluid (BF).

In a particularly advantageous embodiment of the invention, the absorbent body 16; 26 is enclosed by a liquid-permeable membrane 17; 27 having permeation properties which are adapted for providing a controlled permeation rate of the water into the absorbent body during wetting. The liquid-permeable membrane 17, 27 is advantageously constituted of cellophane, a stretched polymer film or the like end, in addition to a cohesive effect, provides a possibility to control the rate at which the absorbent body is wetted and, as a consequence, also the swelling rate of the absorbent body and the lengthening rate of the device. In this embodiment, the liquid-permeable membrane preferably is selected in such a way that only water molecules and no other components of the body fluid can penetrate the membrane. However, it is also conceivable with embodiments where the implantable device according to the invention lacks a liquid-permeable membrane.

In another advantageous embodiment, the absorbent body 16;26, or the absorbent body and the liquid-permeable membrane 17; 27 is/are enclosed by a biodegradable, initially water-impervious, barrier layer as shown in FIG. 1A at 18, which advantageously comprises a hydrophobic material which is sensitive to body enzymes, or a macromolecular material which can be hydrolyzed. Thereby, the barrier layer can be constituted of or comprise for example polylactate or polyurethane-urea (PUU). In this embodiment, the possibilities to control the permeation process and, consequently, also the swelling process of the absorbent body after activation are increased.

The present invention should by no means be regarded as being limited to what has been disclosed in the foregoing in connection with the different embodiments, or to what is shown in the attached drawings, but the scope of the invention is defined by the appended claims.

Accordingly, within the limits of what is allowable for the case in question, it is also conceivable with embodiments where the above-discussed cylinder members and/or the absorbent body does/do not have a circular cross-section.

When embodiments of the device according to the invention where activation and deactivation can be influenced from the outside after implantation are concerned, a method comprising the following steps can be utilized for the lengthening and/or correction:

a device according to the invention having appropriate dimensions and lengthening properties for the tubular skeletal bone In question is selected, the device according to the invention hi Implanted into the skeletal bone using techniques which are well-known to the skilled person, the device is left in its place for 14 days, a lengthening of about 0.5 mm length increase is activated twice a day until the desired lengthening/correction L (mm) is achieved, and the device is left in its place within the skeletal bone for an approximate time of 5×L weeks before the device is removed by means of techniques which arc previously known per se.

In case the intention is to utilize a device according to the invention, the activation and deactivation of which cannot be influenced from the outside, a method comprising the following steps can be utilized:

analysis of the lengthening/correction which is required for the skeletal bone in question, a device according to the invention having appropriate dimensions and lengthening properties is selected, the device is implanted using techniques which are previously known per se, the device is left in its place within the bone for a certain [stabilisation] stabilization time counted from the point in time when the desired lengthening/correction has been achieved, and the device is removed using techniques which are previously known per se.

In both cases, the status of the skeletal bone should be regularly supervised by means of radiographs.

Accordingly, when the swelling process of the absorbent body 16; 16'; 26; 116 is concerned, after the activation having been accomplished by moans of an external signal or the device according to the invention coming into contact with body fluid alter the implantation, the swelling process is controlled from the outside and/or is predetermined by the choice and adaptation of the components included in the device according to the invention, so that the swelling process at least will comprise:

(i) an initial phase during which no swelling takes place and recovery from trauma can take place;

(ii) a lengthening phase during which the device according to the invention at a controlled rate gradually adopts the desired length/shape; and (iii) a healing phase during which no further swelling of the absorbent body takes place and healing/stabilization of the skeletal bone in question can take place.

What is claimed is:

1. An implantable device for lengthening and correcting malpositions of skeletal bones, and said device having an elongate shape comprising a first end, a second end, a length dimension and a cross-sectional dimension, wherein said device further comprises a means for lengthening by bringing said first and second ends into displacement from each other to a predetermined distance between each other after wetting, wherein the means for lengthening comprises an absorbent body, which is arranged for bringing said first and second ends to said predetermined distance by means of a controlled swelling after wetting, while the length dimension increases more than the cross-sectional dimension, wherein the absorbent body is enclosed by a liquid-permeable membrane having permeation properties adapted for providing a controlled permeation rate of water into said absorbent body during wetting.

2. An implantable device according to claim 1, wherein the absorbent body primarily is constituted of a matrix of thermosetting melamine formaldehyde plastic on a needled reinforcement material of HT-rayon and micro-crystalline cellulose as a Filler.

3. An implantable device according to claim 1, wherein the device further comprises first and second cylinder members having closed ends and opposite, open ends, wherein the open end of the first cylinder member is at least partially slidably inserted into the open end of the second cylinder member, so that cylinder members together form at least one internal cavity, wherein the absorbent body is arranged within the internal cavity, and that a back stop device is arranged between the open ends for enabling said closed ends of first and second cylinder members to be irreversibly displaced to the predetermined distance after wetting.

4. An implantable device according to claim 3, wherein the device comprises valves for opening or closing a connection between the absorbent body and the environment surrounding the device, wherein said valves are arranged for being controlled by a means selected from the group consisting of radio raves, ultrasonic, induction and magnetic control when accomplishing the activation and/or a deactivation.

5. An implantable device according to claim 3, wherein the back stop device comprises at least one spring-loaded member of one of the cylinder members which is arranged for mechanical engagement with a member provided with steps of the other cylinder member.

6. An implantable device according to claim 3, wherein the cylinder members are constituted of titanium.

7. An implantable device according to claim 3, wherein the absorbent body comprises cellulose acetate or another superabsorbent.

8. An implantable device according to claim 1, wherein the absorption properties of the absorbent body is accomplished by means of wetting with water originating from a body.

9. An implantable device according to claim 1, wherein a biodegradable, initially water-impervious, barrier layer encloses the absorbent body or the absorbent body and the liquid-permeable membrane.

10. An implantable device according to claim 9, wherein the barrier layer is selected from a hydrophobic material which is sensitive to body enzymes, and a macromolecular material which can be hydrolyzed.

* * * * *